US005753079A

United States Patent [19]

Jenny et al.

[11] Patent Number: 5,753,079
[45] Date of Patent: May 19, 1998

[54] OBTAINING ENHANCED PAPER PRODUCTION USING CATIONIC COMPOSITIONS CONTAINING DIOL AND/OR DIOL ALKOXYLATE

[75] Inventors: Neil A. Jenny, Lake Geneva, Wis.; Robert O. Keys, Columbus, Ohio

[73] Assignee: Witco Corporation, Greenwich, Conn.

[21] Appl. No.: 642,440

[22] Filed: May 3, 1996

Related U.S. Application Data

[63] Continuation-in-part of Ser. No. 430,516, Apr. 27, 1995, Pat. No. 5,686,023, which is a continuation-in-part of Ser. No. 430,528, Apr. 27, 1995, Pat. No. 5,674,832.

[51] Int. Cl.$^6$ .......................... D21H 17/06; D21H 17/07
[52] U.S. Cl. .......................... 162/158; 162/111; 162/173; 162/168.1; 162/164.6
[58] Field of Search .................... 162/158, 179, 162/164.6, 173, 111, 112, 168.1, 169

[56] References Cited

U.S. PATENT DOCUMENTS

| | | | |
|---|---|---|---|
| 2,679,482 | 5/1954 | Ross . | |
| 2,956,025 | 10/1960 | Lew . | |
| 2,997,447 | 8/1961 | Russell et al. . | |
| 3,463,735 | 8/1969 | Stonebraker et al. . | |
| 3,705,113 | 12/1972 | Sharman . | |
| 3,766,062 | 10/1973 | Wixon . | |
| 3,819,522 | 6/1974 | Zmoda et al. . | |
| 4,140,641 | 2/1979 | Ramachandran . | |
| 4,250,269 | 2/1981 | Buckman et al. | 525/6 |
| 4,351,699 | 9/1982 | Osborn, III | 162/112 |
| 4,414,128 | 11/1983 | Goffinet . | |
| 4,441,962 | 4/1984 | Osborn, III | 162/111 |
| 4,454,049 | 6/1984 | MacGilp et al. . | |
| 4,692,277 | 9/1987 | Siklosi . | |
| 5,202,050 | 4/1993 | Culshaw et al. . | |
| 5,334,286 | 8/1994 | Van Phan et al. | 162/158 |
| 5,393,334 | 2/1995 | Hutcheson | 106/199 |
| 5,399,272 | 3/1995 | Swartley et al. . | |
| 5,405,501 | 4/1995 | Phan et al. | 162/127 |
| 5,427,697 | 6/1995 | Swartley . | |
| 5,487,813 | 1/1996 | Vinson et al. . | |

FOREIGN PATENT DOCUMENTS

| | | | |
|---|---|---|---|
| 240727 A2 | 10/1987 | European Pat. Off. . | |
| 3-113099 | 5/1991 | Japan | 162/111 |
| 2 121 449 | 12/1983 | United Kingdom | 162/158 |

OTHER PUBLICATIONS

Gessner H. hawley "The Condensed Chemical Dictionary", tenth Edition, 1981, pp.-505, 1981.
Egan, "Cationic Surface Active Agents as Fabric Softeners", J. Am. Oil. Chemists' Soc., 55:118–121 (Jan. 1978).
"Technical Bulletin Shell Chemical Company", SC:1306–91 Selected pages, Product Bulletin, Dowanol Glycol Ethers Dow Chemical Company.
Product Bulletin, Petro products, pp. 1–9.
Walley, "Fabric Conditioning Agents," Happi, pp. 55–58 (Feb. 1995).

*Primary Examiner*—Peter Chin
*Assistant Examiner*—Jose A. Fortuna
*Attorney, Agent, or Firm*—Scully, Scott, Murphy & Presser

[57] ABSTRACT

Enhanced paper debonding and softening are achieved by producing the paper from an aqueous suspension of fibers which contains one or more cationic agents and one or more compounds of the formula $HO(X-O)_x-R-(O-Y)_y-OH$ wherein each X is ethylene, straight or branched propylene, or straight or branched butylene; x is 0 to 40; each Y is ethylene, straight or branched propylene, or straight or branched butylene; y is 0 to 40; the sum of (x+y) is 0 to 40; and R is saturated straight, branched or cyclic alkylene containing 4 to 12 carbon atoms.

23 Claims, No Drawings and provides as well additional advantages that will become apparent in the following description.

OBTAINING ENHANCED PAPER PRODUCTION USING CATIONIC COMPOSITIONS CONTAINING DIOL AND/ OR DIOL ALKOXYLATE

This application is a continuation-in-part of prior application Ser. No. 08/430,516, filed Apr. 27, 1995, now U.S. Pat. No. 5,686,023 which is a continuation-in-part of Ser. No. 08/430,528, filed Apr. 27, 1995, now U.S. Pat. No. 5,674,832.

BACKGROUND OF THE INVENTION

The present invention relates to liquid compositions useful in the paper industry for debonding and softening of paper fibers, and relates to the uses of those compositions in producing paper.

The present invention relates more particularly to novel compositions for liquid cationic formulations, wherein the ingredients of the composition contribute significantly to the ease of formulation, stability, dispersibility, fluidity and the performance properties of the compositions.

Cationics have achieved widespread usage because of their ability to impart to fabric, (i.e. articles of clothing, textiles, and so forth), paper, hair, and many other substrates, properties including softness to the touch, ease of handling, increased lubricity, and a reduced tendency to carry or pick up static electricity. One form in which cationics are provided is as a liquid, for instance as an emulsion or as a solution/suspension of the desired components. An appropriate controlled amount of the liquid cationic formulation is employed (i.e. added to the head box of a paper making machine, or into the fan pump or a feed line upstream from the headbox, or sprayed onto the wet sheet from which the paper is made, or otherwise depending on the application, as described further herein).

Typically, in the case of the papermaking process, cationics called debonders are generally quaternary salt emulsions in water. These are added (for instance) to the head box wherein the dilute fibers are conditioned with the debonders just prior to being fed onto the papermaking screen. These debonders give improved softness feeling to the paper fibers. In all cases the cationics are added to water to make an emulsion, and then added to the substrate in water or added as a high solids concentrate to the substrate, to impart softness, lubricity, antistatic properties, ease of handling of the substrate and to improve surface appearance.

It is believed that the user finds it to be desirable that the liquid cationic formulation is in the form of a moderately viscous fluid, rather more viscous than water yet still capable of flowing under its own weight; and preferably capable of being poured and sprayed with conventional equipment. Thus, for instance, a formulation that at solids concentrations on the order of 50–80 wt. % exhibits a viscosity such that it is sprayable, and which disperses readily in cold water, such as the present invention, would be desirable in the marketplace. In other cases, the industrial user may want less viscous, fluid emulsions or concentrates that disperse easily, with fine particle sizes.

In the case of paper manufacture, formulations which would be low melting (compared to many materials which must be heated to 90°–120° F.) and are easily dispersed in room temperature water would save time and money in both equipment and production costs. It is particularly desirable to have a cationic formulation which can be supplied to the papermaking facility as a prepackaged, predispersed liquid in a container/dispenser that can be simply "plugged in" to the papermaking equipment (for instance, feeding at a controlled rate into the headbox of a Fourdrinier). The formulation in such a setting needs to stay thoroughly dispersed, without needing auxiliary agitation, regardless of the ambient temperature which depending on the geographical location and climate can range from 80° F. and above to 0° F. and below.

There is a need for cationic formulations, for use in paper debonding and paper softening, which are nonflammable yet easy to handle and disperse in room temperature water. Most quaternary formulations contain isopropanol or ethanol as solvents in order to aid in production and handling. However, volatile solvents such as these are becoming an important environmental issue in states including California and Florida. Thus, a different technique for achieving fluidity and good dispersiblity, while avoiding the use of volatile solvents, is needed. Also, as interest grows in dilutable concentrated product which can be diluted by the customer (e.g. by 3–10 times) to make a regular concentration of the product as used, the need for making such products that are easily dispersible without resort to volatile or flammable solvents is very important.

Thus, there is still a need in the papermaking field for liquid cationic formulations which can be prepared more readily without encountering difficulties such as those described above, and are more concentrated and disperse easily in cold water. There is also a need in this field for cationic formulations which can be manufactured as concentrates, wherein formulators can produce consumer and industrial products easily, quickly and effectively with minimal equipment and heating requirements. There is also a need for products (especially for use in the paper areas) which are not flammable but which avoid the handling and viscosity problems posed by the conventional less flammable substitutes such as propylene glycol, diethylene glycol and the like.

The present invention satisfies the needs identified above, and provides as well additional advantages that will become apparent in the following description.

BRIEF SUMMARY OF THE INVENTION

One aspect of the present invention is a process for producing paper, comprising forming an aqueous suspension of fibers into a sheet and drying the sheet, wherein the aqueous suspension further comprises a quaternary ammonium component and a nonionic component selected from the group consisting of compounds of the formula (1)

$$HO-(X-O)_x-R-(O-Y)_y-OH \qquad (1)$$

and mixtures thereof wherein each X is independently ethylene (i.e., —$C_2H_4$—), straight or branched propylene (i.e., —$C_3H_6$—), or straight or branched butylene (i.e., —$C_4H_8$—); x is 0–40; each Y is ethylene, straight or branched propylene, or straight or branched butylene; y is 0–40; the sum of (x+y) is 0–40; and R is straight, cyclic or branched alkylene containing 4–12 carbon atoms. Preferably, if x and y are both zero then R contains 7 to 12 carbon atoms. In preferred embodiments, the quaternary ammonium component comprises one or more cationic agents, i.e., quaternary ammonium compounds and/or amine salts as described herein, which would impart debonding to the fibers, and/or softening to the paper, even in the absence of the nonionic component defined herein. However, the presence of the nonionic component defined herein in combination with the quaternary ammonium component as defined herein imparts improved debonding and/or softening properties.

Thus, another aspect of the present invention is the process of debonding the fibers in an aqueous suspension of fibers from which paper can be made, comprising adding to the suspension a composition that comprises a quaternary ammonium component and a nonionic component, both as defined herein, which also usually comprises water.

Yet another aspect of the present invention is the process of increasing the softness and absorbance of paper made from an aqueous suspension of fibers, the process comprising adding to the suspension a composition that comprises a quaternary ammonium component and a nonionic component, both as defined herein, which also usually comprises water.

Another aspect of the present invention is paper comprising papermaking fibers and a softening composition which comprises a quaternary ammonium component and a nonionic component as defined hereinabove.

DETAILED DESCRIPTION OF THE INVENTION

The present invention is applicable to the manufacture of paper, and to any of the various particular techniques that may be employed for producing paper, particularly as to paper to be made into products wherein the property of softness is desirable. Examples of such paper products include napkins, toweling, and facial and toilet tissue. Without intending to be bound by any specific production detail, the processes for the manufacture of paper with which the present invention can be carried out include the establishment of a uniform aqueous dispersion of fibers, the formation of that dispersion into a flat sheet, and the drying of the sheet to form paper which can then be rolled, cut, and formed as desired into any of numerous products.

The aqueous dispersion of fibers is obtained by any of the numerous known processes, beginning from pulp of virgin pulpwood, from recycled paper and/or cardboard stock, or mixtures thereof. The pulp is subjected to treatment by any of several conventional processes, to help the establishment of a dispersion of fibers sufficiently finely dispersed to constitute an acceptable dispersion processable into paper. Thus, the pulp can be treated for instance mechanically, chemically, or both, often with the application of heat, to convert it to a processable dispersion. Several chemical processes such as the Kraft process are well-known in this field.

The fibers as that term is used herein include any of a chemical constituency and physical form which can be formed into an aqueous dispersion which can in turn be produced into paper. Generally the fibers are predominantly cellulosic but may also contain lignins, hemi-cellulosics, and other fibrous components derived from synthetic polymers, cloth, and the like.

The aqueous dispersion of fibers can optionally contain any of numerous conventional additives such as sizing, pigments, wet strength resins, dry strength additives, fillers and opacifiers, defoamers, and the like, present in the amount appropriate for achieving the desired function of each such component that is used. One advantage of the present invention is that the softening and debonding provided by this invention overcome to a significant extent the harshness of feel that these additives often impart to paper. This advantage is especially favorable in the case of paper for products such as the aforementioned napkins, toweling and tissue.

The aqueous dispersion of fibers is then formed into a flat sheet, usually by means of a machine specially adapted for this function. Preferably, a Fourdrinier or equivalent machine presenting a wide, flat, porous screen (which preferably moves at a predetermined rate) has at one end a means such as a headbox which contains the aqueous dispersion of fibers and which feeds the dispersion at a controlled rate onto one end of the screen.

The flat sheet formed in this or any equivalent manner still contains a substantial portion of water. As the sheet is carried along on the screen water is removed, by its own weight through the screen and often with the aid of pressure, heat, or both. The sheet can then be treated with other equipment such as heated rollers or the like, which further reduces the moisture content until the sheet is sufficiently dried into paper. Thereafter, the paper is stored, cut and/or otherwise converted in known manner into useful products.

The Diols and Alkoxylates

The compounds of the aforementioned formula (1), sometimes referred to herein as diols and diol alkoxylates, contribute essentially to many of the advantageous properties of the compositions of the present invention. In formula (1), the molecule can comprise no, one or two terminal poly(alkoxy) chains. While, as defined above, each alkoxy unit can be ethoxy, propoxy, or butoxy, a mixture of types of alkoxy groups, or block copolymers composed of a chain of one type of repeating alkoxy unit attached to a chain of a different type of repeating alkoxy unit, are especially contemplated.

The alkylene residue R in formula (1) represents a saturated, straight-chain, branchedchain, or cyclic moiety containing 4 to 12 carbon atoms. It is preferred that R is branched; the term "branched" is intended to encompass structures having one side alkyl chain, more than one side alkyl chain, or one or more side alkyl chains one or more of which is itself branched. Branched structures include cyclic structures substituted with one or more alkyl groups which can be straight or branched. Examples of suitable R groups include —$CH_2CH_2CH_2$—, —$C(CH_3)CH_2$—, —$CH_2CH(CH_3)CH_2$—, —$CH_2C(CH_3)_2CH_2$—, —$CH_2CH(CH_2CH_2CH_2CH_3)$—, —$(CH_2)_6$—, —$CH(CH_2)_2CH(CH_2)_2$—, —$CH_2C(CH_3)_2CH(CH(CH_3)_2)$—, and —$CH_2CH(CH_2CH_3)CH_2CH_2CH_2$—.

In the alkoxylated diols, the number of repeating units in each poly(alkoxy) chain can be up to 40 but it is preferred that each chain contains 1 to 10 repeating alkoxy units or more preferably 1 to 5 alkoxy units. The preferred alkoxy chains are poly(ethoxy), or are composed of 1 to 2 ethoxy units capped with a chain of 1 to 5 propoxy units.

Compounds of the formula (1) defined above are in many instances commercially available. Compounds of formula (1) can be prepared in straightforward manner familiar to those of ordinary skill in this art by obtaining or preparing the corresponding precursor diol of the formula HO—R—OH, and then alkoxylating the precursor diol with a stoichiometrically appropriate number of moles of the desired corresponding alkylene oxide, such as ethylene oxide, propylene oxide, and/or butylene oxide. In those cases where it is desired to alkoxylate only one of the hydroxyl groups on the precursor diol, in some embodiments the alkoxylation will preferentially occur at only one of the hydroxyl groups, particularly where one of them is a primary hydroxyl and the other is a secondary hydroxyl. However, in those cases where both hydroxyl groups on the precursor diol might tend to alkoxylate but alkoxylation at only one of the hydroxyl groups is desired, the hydroxyl group at which alkoxylation is desired not to occur can be protected by preliminarily reacting it with a suitable protecting group such as a lower alkyl moiety or an esterifying substituent. Thereafter, following the alkoxylation, the protecting group is removed in a known manner.

Preferred examples of compounds of the foregoing formula (1) include any one, or mixtures, of 2,2,4-trimethyl-1,3-pentane diol (referred to herein as "TMPD") and/or 2-ethylhexane-1,3-diol, and/or the reaction product of TMPD and/or 2-ethylhexane-1,3diol with 1 to 10 moles of ethylene oxide, and preferably with 1 to 5 moles of ethylene oxide, as well as analogs alkoxylated with other $C_3$ or $C_4$ alkyl oxides or mixtures of any of $C_2$, $C_3$ and/or $C_4$ alkyl oxides. Since the diol which is alkoxylated includes one primary hydroxyl group and one secondary hydroxyl group, the alkoxylation proceeds predominantly at the primary hydroxyl group.

The Quaternaries

The cationic component of the present invention is one compound, or a combination of more than one compound, which compound or combination exhibits or imparts the properties desired to the aqueous suspension of fibers, to paper made from an aqueous suspension of fibers, or both. Those properties include debonding the fibers, and imparting to the paper a number of improved characteristics.

Compounds one or more of which make up the cationic component, are typically quaternary ammonium compounds, amine salts and diamine and triamine counterparts thereof.

As indicated, the present invention and its attendant advantages are realized with any cationic agent and particularly those which are mono- or di-(long chain alkyl) derivatives. Without intending to limit the scope of this invention, the following are provided as examples of cationic agents that can be employed in the present invention. That is, the present invention is intended to extend to compositions containing any other cationic compound that may not be mentioned herein.

Cationic agents usable in the present invention include, but are not limited to, nitrogenous compounds selected from the group consisting of quaternized or acid salt derivatives of:

(i) alkylenediamines including compounds of the formula:

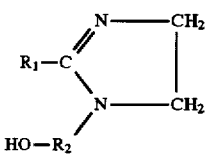

wherein each $R_1$ is an acyclic alkyl or alkylene $C_{12}$–$C_{21}$ hydrocarbon group, each Z is —$(R_2O)_{0-4}H$, or —$R_2H$, and $R_2$ and $R_3$ are divalent $C_1$–$C_6$ alkylene groups;

(ii) substituted imidazoline compounds having the formula:

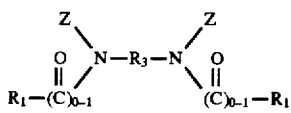

(iii) substituted imidazoline compounds having the formula:

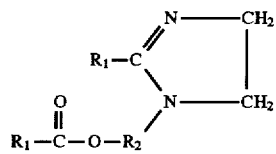

wherein $R_1$ and $R_2$ are defined as above;

(iv) reaction products of higher fatty acids with alkylenetriamines in, e.g., a molecular ratio of about 2:1, said reaction products containing compounds of the formula:

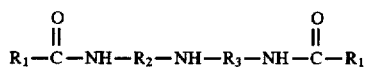

wherein $R_1$, $R_2$ and $R_3$, are defined as above;

(v) substituted imidazoline compounds having the formula:

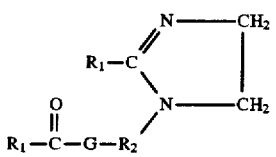

wherein G is —O— or —NH— and $R_1$ and $R_2$ are defined as above; and mixtures thereof.

Preferred examples of compounds of formula (i) are those derived from hydrogenated tallow fatty acids and the hydroxyalkylalkylenediamine N-2-hydroxyethylethylenediamine, such that $R_1$ is an aliphatic $C_{15}$–$C_{21}$ hydrocarbon group, and $R_2$ and $R_3$ are divalent ethylene groups.

A preferred example of compounds of formula (ii) is stearic hydroxyethyl imidazoline wherein $R_1$ is an aliphatic $C_{17}$ hydrocarbon group and $R_2$ is a divalent ethylene group.

A preferred example of compounds of formula (iv) is N,N"-ditallowalkanoyldiethylenetriamine where $R_1$ is an aliphatic $C_{15}$–$C_{21}$ hydrocarbon group and $R_2$ and $R_3$ are divalent ethylene groups.

A preferred example of compounds of formula (v) is 1-tallowamidoethyl-2-tallowimidazoline wherein $R_1$ is an aliphatic $C_{15}$–$C_{21}$ hydrocarbon group and $R_2$ is a divalent ethylene group.

Both N,N"-ditallowalkanoyldiethylenetriamine and 1-tallowethylamido-2-tallowimidazoline are reaction products of tallow fatty acids and diethylenetriamine, and are precursors of the cationic agent methyl-1-tallowamidoethyl-2-tallowimidazolinium methylsulfate which is sold by Witco Corporation under the trade name Varisoft® 475.

Compositions containing Varisoft® 475, and their use in paper manufacture, are a preferred embodiment of the present invention, as are compositions and methods employing the dioleyl analogs of the di-tallow compounds. Thus, compositions containing methyl-1-oleylamidoethyl-2-oleyl imidazolinium methylsulfate which is (available from Witco Corp. as Varisoft® 3690), and their use in paper manufacture, are also preferred. Highly advantageous formulations containing over 60 wt. % and even up to 80 wt. % solids can be formed using one or both of these preferred cationic components and 20–40 wt. % of a nonionic component as defined herein.

Other useful softening agents include cationic nitrogenous quaternary ammonium compounds and salts. In the cationic nitrogenous salts herein, the anion $A^{\ominus}$ provides electrical neutrality. Most often, the anion used to provide electrical neutrality in these salts is a halide, such as chloride, bromide, or iodide. However, other anions can be used, such as methylsulfate, ethylsulfate, acetate, formate, sulfate, carbonate, and the like. Chloride and methylsulfate are preferred herein as the anion $A^-$.

One type of cationic compounds are those containing one long chain acyclic aliphatic $C_8-C_{22}$ hydrocarbon group, selected from the group consisting of:

(vi) acyclic quaternary ammonium salts having the formula:

$$\left[ \begin{array}{c} R_5 \\ | \\ R_4-N-R_5 \\ | \\ R_6 \end{array} \right]^{\oplus} A^{\ominus}$$

wherein $R_4$ is an acyclic aliphatic $C_8-C_{22}$ hydrocarbon group, alkyl, benzyl or $(C_4-C_{18}$ alkyl)—$(OCH_2CH_2)_{2-3}$—, $R_5$ and $R_6$ are $C_1-C_4$ saturated alkyl or hydroxyalkyl groups and $A^{\ominus}$ is an anion (wherein the derivative in which $R_4$ is benzyl and $A^{\ominus}$ is chloride is an effective slimicide useful in papermaking operations);

(vii) substituted imidazolinium salts having the formula:

$$\begin{array}{c} N\!-\!-\!-\!CH_2 \\ R_1-C \diagup \quad \quad | \quad \quad A^- \\ \diagdown \!N\!-\!-\!-\!CH_2 \\ \diagup \diagdown \\ R_7 \quad H \end{array}$$

wherein $R_1$ is an acyclic aklyl or alkylene $C_{12}-C_{21}$ hydrocarbon group, $R_7$ is hydrogen or a $C_1-C_4$ saturated alkyl or hydroxyalkyl group, and A is an anion;

(viii) substituted imidazolinium salts having the formula:

$$\begin{array}{c} N\!-\!-\!-\!CH_2 \\ R_1-C \diagup \quad \quad | \quad \quad A^- \\ \diagdown \!N\!-\!-\!-\!CH_2 \\ \diagup \diagdown \\ HOR_2 \quad R_5 \end{array}$$

wherein $R_1$, $R_2$, $R_5$ and A are as defined above;

(ix) diquaternaries of the formula $(R^1N(Z_2)\!-\!(CH_2)_{2-6}\!-\!N(Z_3))^{-2} \cdot 2A^-$ wherein $R^2$ and each Z are independently as defined above;

(x) alkylpyridinium salts having the formula:

$$\left[ R_4-N \diagup\!\!\!\diagdown \right]^{\oplus} A^{\ominus}$$

wherein $R_4$ is an acyclic aliphatic $C_8-C_{22}$ hydrocarbon group and $A_{\ominus}$ is an anion; and (xi) alkanamide alkylene pyridinium salts having the formula:

$$\left[ \begin{array}{c} O \\ \| \\ R_1-C-NH-R_2-N \diagup\!\!\!\diagdown \end{array} \right]^{\oplus} A^{\ominus}$$

wherein $R_1$ is an acyclic aliphatic $C_{12}-C_{21}$ hydrocarbon group, $R_2$ is a divalent $C_1-C_6$ alkylene group, and $A_{\ominus}$ is an anion; and mixtures thereof. Examples of compound (vi) are the monoalkyltrimethylammonium salts such as monotallowtrimethylammonium chloride, mono(hydrogenated tallow)-trimethylammonium chloride, palmityltrimethylammonium chloride and soyatrimethylammonium chloride, sold by Witco Corporation under the trade names Adogen 471, Adogen 441, Adogen 444, and Adogen 415, respectively. In these compounds, $R_4$ is an acyclic aliphatic $C_{16}-C_{18}$ hydrocarbon group, and $R_5$ and $R_6$ are methyl groups. Mono(hydrogenated tallow) trimethylammonium chloride and monotallowtrimethylammonium chloride are preferred. Other examples of compound (vi) are behenyltrimethylammonium chloride wherein $R_4$ is a $C_{22}$ hydrocarbon group and sold under the trade name Kemamine® Q2803-C by Humko Chemical Division of Witco Corporation; soyadimethylethylammonium ethylsulfate wherein $R_4$ is a $C_{16}-C_{18}$ hydrocarbon group, $R_5$ is a methyl group, $R_6$ is an ethyl group, and $A^-$ is an ethylsulfate anion; and methyl bis(2-hydroxyethyl) octadecylammonium chloride wherein $R_4$ is a $C_{18}$ hydrocarbon group, $R_5$ is a 2-hydroxyethyl group and $R_6$ is a methyl group.

An example of compound (viii) is 1-ethyl-1-(2-hydroxyethyl)-2-isoheptadecylimidazolinium ethylsulfate wherein $R_1$ is a $C_{17}$ hydrocarbon group, $R_2$ is an ethylene group, $R_5$ is an ethyl group, and $A^-$ is an ethylsulfate anion.

Other fabric softening agents useful in the present invention include cationic nitrogenous salts having two or more long chain acyclic aliphatic $C_8-C_{22}$ hydrocarbon groups or one said group and an arylalkyl group. Examples include:

(xii) acyclic quaternary ammonium salts having the formula:

$$\left[ \begin{array}{c} R_4 \\ | \\ R_4-N-R_5 \\ | \\ R_8 \end{array} \right]^{\oplus} A^{\ominus}$$

wherein each $R_4$ is an acyclic aliphatic $C_8-C_{22}$ hydrocarbon group, $R_5$ is a $C_1-C_4$ saturated alkyl or hydroxyalkyl group, $R_8$ is selected from the group consisting of $R_4$ and $R_5$ groups, and $A^{\ominus}$ is an anion defined as above;

(xiii) diamido quaternary ammonium salts having the formula:

$$\left[ \begin{array}{ccccc} O & & R_5 & & O \\ \| & & | & & \| \\ R_1-C-NH-R_2-N-R_2-NH-C-R_1 \\ & & | & & \\ & & R_9 & & \end{array} \right]^{\oplus} A^{\ominus}$$

wherein each $R_1$ is an acyclic alkyl or alkylene $C_{12}-C_{21}$ hydrocarbon group, each $R_2$ is a divalent alkylene group having 1 to 3 carbon atoms, $R_5$ and $R_9$ are $C_1-C_4$ saturated alkyl or hydroxyalkyl groups, and $A^{\ominus}$ is an anion;

(xiv) alkoxylated diamido quaternary ammonium salts having the formula:

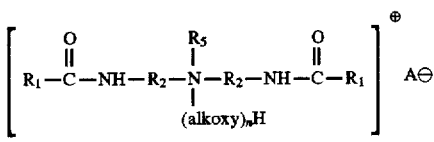

wherein n is equal to 1 to about 5(alkoxy) is ethoxy or propoxy, and $R_1$, $R_2$, $R_5$ and $A^\ominus$ are as defined above;

(xv) quaternary ammonium compounds having the formula:

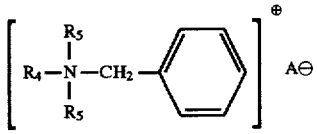

wherein each $R_4$ is an acyclic aliphatic $C_8$–$C_{22}$ hydrocarbon carbon group, each $R_5$ is a $C_1$–$C_4$ saturated alkyl or hydroxyalkyl group, and $A^\ominus$ is an anion;

(xvi) amide-substituted imidazolinium salts having the formula:

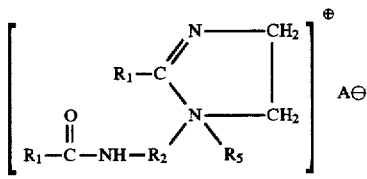

wherein each $R_1$ is an acyclic aliphatic $C_{12}$–$C_{21}$ hydrocarbon group, $R_2$ is a divalent alkylene group having 1 to 3 carbon atoms, and $R_5$ and $A^\ominus$ are as defined above or $R^5$ is —H; and (xvii) ester-substituted imidazolinium salts having the formula:

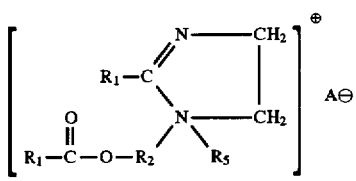

wherein $R_1$, $R_2$, $R_5$ and $A^\ominus$ are as defined above; and mixtures thereof.

Examples of compound (xii) are the well-known dialkyldimethylammonium salts such as ditallowdimethylammonium chloride, di-hard tallowdimethylammonium methylsulfate (a particularly preferred embodiment, commercially available as "Varisoft 137" from Witco Corp.), di(hydrogenated tallow)dimethylammonium chloride, distearyldimethylammonium chloride, dibehenyldimethylammonium chloride. Di(hydrogenated tallow) dimethylammonium chloride and ditallowdimethylammonium chloride are preferred. Examples of commercially available dialkyldimethylammonium salts usable in the present invention are di(hydrogenated tallow)dimethylammonium chloride (trade name Adogen 442), ditallowdimethylammonium chloride (trade name Adogen 470), distearyldimethylammonium chloride (trade name Arosurf TA-100), all available from Witco Corporation. Dibehenyldimethylammonium chloride wherein $R_4$ is an acyclic aliphatic $C_{22}$ hydrocarbon group is sold under the trade name Kemamine Q-2802C by Humko Chemical Division of Witco Corporation.

Examples of compound (xiii) are methylbis (tallowamidoethyl) (2-hydroxyethyl)ammonium methylsulfate and methylbis(hydrogenated tallowamidoethyl)(2-hydroxyethyl)ammonium methylsulfate wherein $R_1$ is an acyclic aliphatic $C_{15}$–$C_{17}$ hydrocarbon group, $R_2$ is an ethylene group, $R_5$ is a methyl group, $R_9$ is a hydroxyalkyl group and $A^-$ is a methylsulfate anion; these materials are available from Witco Corporation under the trade names Varisoft 222 and Varisoft 110, respectively.

An example of compound (xiv) is methyl bis (tallowamidoethyl) 2-hydroxypropylammonium methylsulfate, commercially available as "Varisoft 238" (Witco).

An example of compound (xv) is dimethylstearylbenzylammonium chloride wherein $R_4$ is an acyclic aliphatic $C_{18}$ hydrocarbon group, $R_5$ is a methyl group and $A^-$ is a chloride anion, which is sold under the trade name Varisoft SDC by Witco Corporation.

Examples of compound (xvi) are 1-methyl-1-tallowamidoethyl-2-tallowimidazolinium methylsulfate and 1-methyl-1-(hydrogenated tallowamidoethyl)-2-(hydrogenated tallow) imidazolinium methylsulfate wherein $R_1$ is an acyclic aliphatic $C_{15}$–$C_{17}$ hydrocarbon group, $R_2$ is an ethylene group, $R_5$ is a methyl group and $A^-$ is a chloride anion; they are sold under the trade names Varisoft 475 and Varisoft 445 respectively, by Witco. As mentioned hereinabove, the di-oleyl analogs such as the aforementioned "Varisoft 3690" are also highly preferred.

Additional examples of fabric softening compounds useful in the present invention include (xviii) compounds characterized by the formula:

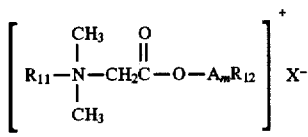

wherein $R_{11}$ is a radical selected from the group consisting of (a) straight chain aliphatic hydrocarbon radicals each of which contains from 12 through 24 carbon atoms, (b) ether radicals each of which has the structure: $R_{13}O(CH_2O)_y$—, (c) amide radicals each of which has the structure:

and (d) ester radicals each of which has the structure:

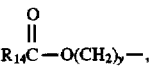

$R_{12}$ is a straight chain aliphatic hydrocarbon radical containing from 12 to 32 carbon atoms, $R_{13}$ is a straight chain aliphatic hydrocarbon radical containing from 8 to 18 carbon atoms, $R_{14}$ is a straight chain aliphatic hydrocarbon radical containing from 7 to 17 carbon atoms, A is an alkoxy radical containing one oxygen atom and either two or three carbon atoms, X is an atom selected from the group consisting of bromine and chlorine, m is an integer of from 1 through 12, and y is an integer which is either 2 or 3.

Yet additional examples of fabric softening compounds useful in the present invention include (xix) compounds having the formula:

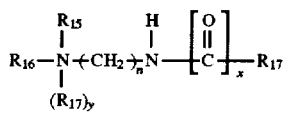

wherein each $R_{15}$ is selected from the group consisting of hydrogen and $C_1$–$C_4$ alkyl, each $R_{16}$ is selected from the group consisting of $C_1$–$C_4$ alkyl and

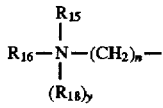

each $R_{17}$ is selected from the group consisting of $C_8$–$C_{28}$ alkyl and alkenyl groups, each $R_{18}$ is selected from the group consisting of hydrogen and $C_1$–$C_4$ alkyl, each y is 0 or 1, x is 0 or 1 and each n is from 1 to 6;

(xx) amides represented by the formula:

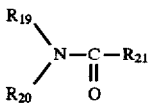

wherein $R_{19}$ and $R_{20}$ are, selected independently, $C_{1-22}$ alk(en)yl aryl, or alkyl aryl groups, $R_{21}$ is hydrogen, or a $C_{1-22}$ alk(en)yl, aryl or alkyl-aryl group, or is O—$R_4$, wherein $R_{22}$ is a $C_{1-22}$ alk(en)yl, aryl or alkyl-aryl group, and $R_{21}$ and $R_{22}$ possibly containing 1 to 10 ethylene oxide units, or functional groups selected from hydroxy, amine, amide, ester, and ether groups; the aryl groups being possibly derived from hetero-cyclic compounds; at least one of the $R_{19}$ and $R_{20}$ groups contains 10 or more carbon atoms; the sum of carbon atoms in $R_{19}+R_{20}+R_{21}$ is equal to or greater than 14. Preferably, the sum of carbon atoms in $R_{19}+R_{20}$ is equal to or greater than 16.

Such species include N,N-ditallow acetamide, N,N-dicoconut acetamide, N,N-dioctadecyl propanamide, N-dodecyl, N-octadecyl acetamide, N-hexadecyl, N-dodecyl butanamide, N,N-ditallow benzamide, N,N-dicoconut benzamide, and N,N-ditallow 2-phenyl acetamide.

Additional fabric softening compounds useful in the present invention include all ester-quaternaries, including but not limited to:

(xxi) compounds of any of the formulas

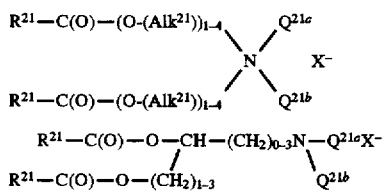

wherein each $R^{21}$ is independently a saturated or unsaturated alkyl or alkylene radical containing 12 to 22 carbon atoms;

$Q^{21a}$ and $Q^{21b}$ are alkyl containing 1 to 4 carbon atoms or benzyl, —$CH_2CH_2OH$, or —$CH_2CH(OH)CH_3$, or $Q^{21a}$ can be $R^{21}$—$C(O)$—$(O$—$(Alk^{21}))_{1-4}$—;

each $Alk^{21}$ is independently $C_2H_4$, $C_3H_6$ or $C_4H_8$;

$R^2$ is alkyl containing 1 to 4 carbon atoms or benzyl, —$CH_2CH_2OH$ or —$CH_2CH(OH)CH_3$; and $X^-$ is an anion as above, preferably chloride or methyl sulfate;

(xxii) compounds of the formula

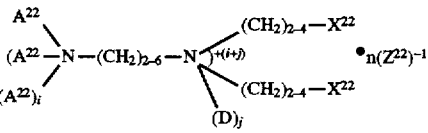

wherein each $A^{22}$ is the same or different and each is alkyl containing up to 3 carbon atoms, benzyl, or $H(Alk^{22}$—$O)_{1-3}$—$Alk^{22}$—wherein each $Alk^{22}$ signifies —$CH_2CH_2$—, —$CH(CH_3)CH_2$—, or —$CH_2CH(CH_3)$—, provided further that one of the $A^{22}$ can be hydrogen;

D is methyl, ethyl, propyl, —$(CH_2)_{1-3}COO^-$, benzyl or hydrogen;

i is 0 or 1 and j is 0 or 1, provided that the sum of (i+j) is 1 or 2;

each $X^{22}$ is a straight or branched saturated or unsaturated aliphatic group containing up to 3 carbon-carbon double bonds and containing 11 to 23 carbon atoms;

n is (two minus the number of —$(CH_2)_{1-3}COO^-$ substituents present); and $Z^{22}$ is an anion;

(xxiii) compounds of the formula

wherein each $R^{23}$ is independently straight or branched alkyl or alkenyl containing 8 to 22 carbon atoms;

$R^{23a}$ is straight or branched alkyl or hydroxyalkyl containing 1 to 3 carbon atoms, benzyl, or —$C_2H_4OC(O)R_4$ wherein $R^4$ is straight or branched alkyl or alkenyl containing 8 to 22 carbon atoms;

$R^{23b}$ is H, —$CH_3$, —$C_2H_5$ or benzyl; and $X^-$ is an anion;

(xxiv) compounds of the formula

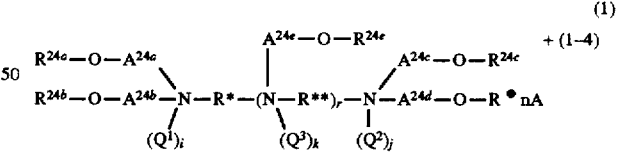

wherein each of $R^*$ and $R^{**}$ is independently a linear, branched or cyclic alkyl group containing 2 to 12 carbon atoms, wherein no two nitrogen atoms are separated by fewer than 2 carbon atoms;

each of $A^{24a}$, $A^{24b}$, $A^{24c}$, $A^{24d}$ and each occurrence of $A^{24e}$ is independently straight or branched containing 2 to 4 carbon atoms;

each of $R^{24a}$, $R^{24b}$, $R^{24c}$, and $R^{24d}$ and each occurrence of $A^{24e}$ is independently straight or branched containing 2 to 4 carbon atoms;

each of $R^{24a}$, $R^{24b}$, $R^{24c}$, and $R^{24d}$ and each occurrence of $R^{24e}$ is independently —H or $R^4C(=O)$— wherein $R^4$ is straight or branched alkyl or alkenyl containing 9 to 21 carbon atoms and 0 to 4 carbon— carbon double bonds; provided that at least one of $R_{24a}$, $R^{24b}$, $R_{24c}$, and $R^{24d}$ or $R_{24e}$ is $R^AC(=O)-$; each of $Q^1$, $Q^2$, and $Q^3$ is $-CH_3$, $-C_2H_5$, or $-CH_2CH_2COOH$;

r is 0–2;

i is 0–1, j is 0–1, each k is 0–1 and the sum of (i+j+k) is 1–4; or r is zero, $R^*$ is $-CH_2CH_2-$, and $Q^1$ and $Q^2$ taken together form $-CH_2CH_2-$;

A is an anion; and n is the number of moles of A needed to give the compound of formula (xxiv) zero net charge. A preferred example is partially or fully quaternized, partially or fully esterified, derivatives of hexamethylene diamine.

(In the foregoing, "Adogen", "Arosurf" and "Varisoft" are trademarks of Witco Corp.)

The cationic compositions used in the present invention usually also contain water but are diluted into or by water in application.

The amounts of the cationic quaternary component, of the nonionic components corresponding to formula (1), and water, can vary within relatively large ranges, depending upon the degree of concentration of the components desired, and depending also on the particular characteristics of the particular components selected. The cationic quaternary component should be present in an amount at least sufficient to afford the desired effect (i.e. paper softening and/or paper debonding, as the case may be) and can be present in amounts substantially higher representing commercial concentrations on the order of 5–25 wt. % up to amounts on the order of 30 percent or higher, up to 60, 70, 80 or even 90 wt. % of the composition. These higher contents represent concentrates from which useful compositions can be formulated upon dilution due to their dispersibility in water, or used as is, if desired.

Optionally, there can be included other components, such as other nonionic compounds, which lower the viscosity of the composition further and make it easier for the composition to be applied topically to the web of paper making fibers, for instance by spraying.

The component of formula (1) is present in an amount sufficient to form with the cationic component a phase-stable, water-dispersible formulation. In general, satisfactory amounts of the one or more compounds of formula (1) correspond to a weight ratio with respect to the amount of quaternary component present of 1:30 to 5:1 (diol or diol alkoxylates:quaternary) and preferably 1:10 to 1:1.

Preferably water is also present, in which case the quaternary component generally comprises 5 wt. % to 80 wt. % of the aqueous composition, and preferably 30–60 wt. % to 70 wt. % thereof; the nonionic component of formula (1) comprises 5 wt. % to 50 wt. % of the aqueous formulation, and preferably 10–25 wt. % to 40 wt. %.

Compositions having the foregoing characteristics can readily be prepared by simply stirring together in appropriate equipment the diol and/or diol alkoxylate component, with the one or more compounds constituting the cationic component, into water, along with any other desired additives.

The compositions can be used in any of several ways. One preferred way is to add the composition directly into the aqueous suspension of fibers before the suspension is formed into a flat sheet. In this embodiment, after the addition, the composition containing the cationic quaternary component comprises 0.01 wt. % to 0.05 wt. % of the aqueous suspension, and preferably 0.02 wt. % to 0.04 wt. % thereof, by weight of the amount of fibers present.

Spraying the composition from above the sheet onto the sheet is the preferred application technique. Other application techniques include rolling or brushing, but these are less preferred because they would risk disturbing the integrity of the wet sheet. The application rate should be calculated to provide to the suspension, amounts of quaternary and nonionic components per weight of suspension within the aforementioned ranges.

Properties: The Compositions Themselves

The compositions of the present invention afford a number of advantages not heretofore contemplated. One advantage is ease of formulation of these cationic compositions. Conventionally, emulsion-based cationic formulations can be made to a concentration of up to about 25 wt. % solids, employing high shear and requiring the addition of a salt such as calcium chloride for viscosity control. Solvent based cationic formulations can be made conventionally containing about 40 to about 60 wt. % solids, but often go through a gel-like phase which is very difficult to disperse, such that an acceptably uniform dispersion of the cationic component can be impossible to achieve. They normally require large levels (e.g. 10% or more) of flammable solvent such as isopropanol or ethanol, and/or hexylene glycol or propylene glycol, to formulate.

On the other hand, compositions prepared in accordance with the present invention exhibit a noticeable ease of dispersibility in water at any concentration level and can be thinned by adding $CaCl_2$ to form fluid formulations. This is quite unique compared to those compositions outside the scope of the present invention requiring additions of e.g. isopropanol and/or ethanol and/or hexylene glycol, which revert back to the emulsion when salts are added. Much higher levels of alcohol and shortchained glycols are needed to maintain fluidity in such compositions. As much as 2 to 5 times more of such conventional solvents or coupling agents are needed for acceptable fluidity than is the case using diols and diol alkoxylates in accordance with the present invention. In addition, the compositions of the present invention do not readily gel when added to water for purposes of dilution. Thus, products of a useful concentration can be prepared from concentrates very easily by simply dispersing an appropriate amount of the concentrate into room temperature water.

The ease of formulation and dispersibility has other beneficial effects, including reduction in heating costs for formulators (who conventionally must heat the blend of components to help achieve the desired uniformity of distribution), and reduction in the amount of energy expended in mixing and transport. These features make it feasible to sell highly concentrated cationic formulations directly to the user, who prepares products having the concentrations conventionally employed from the concentrate by diluting an appropriate small quantity of concentrate with tap water.

Properties in Use of the Compositions

The compositions used in accordance with the present invention also provide numerous advantageous properties to the aqueous suspension of fibers and to the paper made therefrom.

The compositions used in this invention reduce the surface tension on and within the interstices of the fibers, thereby debonding them yet also permitting them to mesh together more closely, thus providing a stronger sheet of paper. Tensile strength of the paper is lowered, thereby imparting improved enhanced softening to the paper. Paper products made in this way such as toweling, napkins, and facial and toilet tissue, exhibit increased water absorbency as well.

The following examples, which are intended for purposes of illustration and not intended to limit the scope of the protection sought for the invention described herein:

EXAMPLE 1

Preparation of Diol Alkoxylate

To a 2-liter Parr reactor was charged 438 grams (3.0 moles) of 2,2,4-trimethyl-1,3-pentane diol and 0.54 grams (0.1 wt. %) of potassium hydroxide. The reactor was sparged with nitrogen and evacuated three times. After heating the contents to 100° C. under vacuum, the reactor was pressured to 10 psia with nitrogen, and heated to 150° C.

Ethylene oxide (264 grams, 6.0 moles) was added over one hour at 150°–160° C. and 50–60 psi. After an additional one hour reaction time, the contents were cooled to 100° C. and a vacuum was pulled to remove any residual ethylene oxide. The product was a clear liquid which had a hydroxyl value of 428 determined by acetylation on a hotplate and titration using KOH (Reference: ASTM Test E222, Method B).

EXAMPLE 2

The following are examples of formulations which can be used in accordance with the present invention.

| FORMULATION A | |
|---|---|
| Component | % by Weight |
| Dimethylbis (softtallowamidoethyl)-2-hydroxyethylammoniummethylsulfate ("Varisoft 222", Witco Corp.) | 80.0 |
| Diol alkoxylate produced by ethoxylating 2,2,4-trimethyl-1,3 pentane diol with 2-moles of ethylene oxide | 20.0 |

This product is a non-aqueous concentrate which is readily dispersible in water at a temperature down to 45° F. Such dispersion produces readily a homogeneous, liquid cationic composition which is uniform in appearance. This product can be diluted, or used as is, in paper manufacture.

| FORMULATION B | |
|---|---|
| Component | % by Weight |
| Methyl-1-oleylamidoethyl-2-oleylimidazoliniummethylsulfate ("Varisoft 3690", Witco Corp.) | 75.0 |
| Diol alkoxylate produced by ethoxylating 2,2,4-trimethyl-1,3-pentanediol with 2 moles of ethylene oxide | 25.0 |

The indicated components were blended together at room temperature, which readily produced a liquid cationic formulation, useful as a paper debonder having a relatively high concentration of active ingredient and which exhibited a homogeneous, uniform appearance.

Among the advantages of the present invention is the high degree of dispersibility in water, even cold or room temperature water, and the resultant ability to formulate from a more highly concentrated form to any target concentration level in water (even room temperature) regardless of temperature with only minimal agitation. Other advantages include low odor and high cost effectiveness compared to conventional compositions. The lack of formation of a gel phase during dilution or dispersion of the material in water is believed to be due to the material forming very fine particles when added to cold water; this feature also provides freedom from having to add salts for adjustment of viscosity.

Cationic emulsions are normally unstable, especially when subjected to freezing and thawing, and have shelf lives of only 3–5 months. On the other hand, emulsions utilizing diol or diol alkoxylate of formula (1) exhibit much longer-term stabilities and better stability against freeze-thaw cycles. They also show good viscosity stability as well in dispersions up to about 10–15 wt. % in most cationic quaternary systems.

Additional Practical Exemplification

Laboratory work with compositions according to the present invention has demonstrated numerous specific advantageous aspects including, but not limited to, those set forth as follows.

| PAPER DEBONDERS | |
|---|---|
| Ingredient | Amount (wt. %) |
| A | |
| Di (hard tallow) dimethyl ammonium methyl sulfate | 40–60 |
| TMPD | 10–25 |
| TMPD × 2-mole ethoxylate | 10–25 |
| Water | 5–15 (melts at 75–80° F.; dispersible in 85° F. water) |
| B | |
| Methyl-1-oleyl amidoethyl-2-oleyl imidazolinium methylsulfate | 60–80 |
| TMPD × 1-mole ethoxylate | 20–40 |

What is claimed is:

1. A process for producing paper, comprising forming an aqueous suspension of fibers into a sheet and drying the sheet, wherein the aqueous suspension comprises 0.01 to 0.05 wt. % of a quaternary ammonium component, and a nonionic component which is present in an amount corresponding to a weight ratio of 1:30 to 5:1 with respect to said quaternary ammonium component and which is selected from the group consisting of compounds of the formula

HO—R—OH and mixtures thereof wherein

R is saturated, straight, branched or cyclic alkylene containing 7 to 12 carbon atoms.

2. A process in accordance with claim 1 wherein R is branched noncyclic alkylene containing 7 to 9 carbon atoms.

3. A process in accordance with claim 1 wherein said nonionic component comprises one or both of 2,2,4-trimethyl-1,3-pentane diol and 2-ethylhexane-1,3-diol.

4. A process in accordance with claim 1 wherein said nonionic component comprises 2,2,4-trimethyl-1,3-pentane diol.

5. A process for producing paper, comprising forming an aqueous suspension of fibers into a sheet and drying the sheet, wherein the aqueous suspension comprises 0.01 to 0.05 wt. % of a quaternary ammonium component, and a nonionic component which is present in an amount corresponding to a weight ratio of 1:30 to 5:1 with respect to said quaternary ammonium component and which comprises a compound of formula (1)

$$HO(X-O)_x-R(O-Y)_y-OH \quad (1)$$

and mixtures thereof wherein each X is independently ethylene, straight or branched propylene, or straight or branched butylene, x is 0 to 40;

each Y is ethylene, straight or branched propylene, or straight or branched butylene;

y is 0 to 40; and

R is saturated, straight, branched or cyclic alkylene containing 4 to 12 carbon atoms wherein one or both of x and y is greater than zero.

6. A process in accordance with claim 5 wherein said nonionic component comprises a compound of formula (1) wherein each X, if x is greater than zero, and each Y, if y is greater than zero, is ethylene.

7. A process in accordance with claim 5 wherein said nonionic component comprises a compound of formula (1) wherein the sum of (x+y) is in the range from 1–10.

8. A process in accordance with claim 7 wherein said nonionic component comprises a compound of formula (1) wherein each X, if x is greater than zero, and each Y, if y is greater than zero, is ethylene.

9. A process in accordance with claim 5 wherein said nonionic component comprises a compound of formula (1) wherein the sum of (x+y) is in the range from 2–5.

10. A process in accordance with claim 5 wherein said nonionic component comprises a compound of formula (1) wherein R is $$-CH_2-C(CH_3)_2-\overset{|}{CH}-CH(CH_3)-CH_3 \text{ or}$$

$$-CH-CH(CH_2CH_3)-\overset{|}{CH}-CH_2-CH_2-CH_3.$$

11. A process in accordance with claim 5 wherein said nonionic component comprises a compound of formula (1) wherein R is $$-CH_2-C(CH_3)_2-\overset{|}{CH}-CH(CH_3)-CH_3.$$

12. A process in accordance with claim 11 wherein said nonionic component comprises a compound of formula (1) wherein R is $$-CH_2-C(CH_3)_2-\overset{|}{CH}-CH(CH_3)-CH_3$$

and each X and Y present is ethylene.

13. A process in accordance with claim 12 wherein said nonionic component comprises a compound of formula (1) wherein R is $$-CH_2-C(CH_3)_2-\overset{|}{CH}-CH(CH_3)-CH_3,$$

and the sum of (x+y) is in the range from 1–10.

14. A process in accordance with claim 11 wherein said nonionic component comprises a compound of formula (1) wherein R is $$-CH_2-C(CH_3)_2-\overset{|}{CH}-CH(CH_3)-CH_3,$$

and the sum of (x+y) is in the range from 1–10.

15. A process in accordance with claim 5 wherein said quaternary ammonium component comprises di(hydrogenated tallow) dimethyl ammonium methyl sulfate.

16. A process in accordance with claim 5 wherein said quaternary ammonium component comprises methyl-1-oleylamidoethyl-2-oleyl-imidazolinium methylsulfate.

17. A process in accordance with claim 5 wherein said quaternary ammonium component comprises methyl-1-tallowamidoethyl-2-tallow-imidazolinium methylsulfate.

18. A process in accordance with claim 5 wherein said quaternary ammonium component comprises one or more compounds selected from the group consisting of compounds of any of the formulas

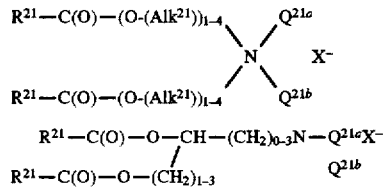

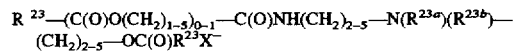

$$R^{23}-(C(O)O(CH_2)_{1-5})_{0-1}-C(O)NH(CH_2)_{2-5}-N(R^{23a})(R^{23b})-(CH_2)_{2-5}-OC(O)R^{23}X^-$$

wherein each $R^{21}$ is independently a saturated or unsaturated alkyl or alkylene radical containing 12 to 22 carbon atoms;

$Q^{21a}$ and $Q^{21b}$ are alkyl containing 1 to 4 carbon atoms or benzyl, $-CH_2CH_2OH$, or $-CH_2CH(OH)CH_3$, or $Q^{21a}$ can be $R^{21}-C(O)-(O-(Alk^{21}))_{1-4}-$;

each $Alk^{21}$ is independently $C_2H_4$, $C_3H_6$ or $C_4H_8$;

each $R^{23}$ is independently straight or branched alkyl or alkenyl containing 8 to 22 carbon atoms;

$R^{23a}$ is straight or branched alkyl or hydroxyalkyl containing 1 to 3 carbon atoms, benzyl, or $-C_2H_4OC(O)R_4$ wherein $R^4$ is straight or branched alkyl or alkenyl containing 8 to 22 carbon atoms;

$R^{23b}$ is H, $-CH_3$, $-C_2H_5$ or benzyl; and $X^-$ is an anion.

19. A process for producing paper, comprising forming an aqueous suspension of fibers into a sheet and drying the sheet, wherein the aqueous suspension comprises 0.01 to 0.05 wt. % of a quaternary ammonium component, and a nonionic component which is present in an amount corresponding to a weight ratio of 1:30 to 5:1 with respect to said quaternary ammonium component and which is selected from the group consisting of compounds of the formula $$HO-R-OH$$

and mixtures thereof wherein

R is saturated, straight, branched or cyclic alkylene containing 7 to 12 carbon atoms, and the quaternary ammonium component is selected from the group consisting of di(hydrogenated tallow) dimethyl ammonium methyl sulfate, methyl-1-oleylamidoethyl-2-oleyl-imadazolinium methylsulfate, methyl-1-tallowamidoethyl-2-tallow-imadazolinium methylsulfate, and compounds of any of the formulas

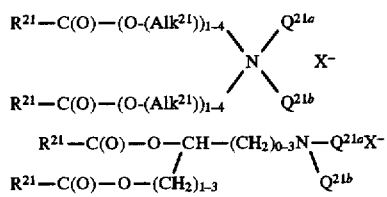

$$R^{23}-(C(O)O(CH_2)_{1-5})_{0-1}-C(O)NH(CH_2)_{2-5}-N(R^{23a})(R^{23b})-(CH_2)_{2-5}-OC(O)R^{23}X^-$$

wherein each $R^{21}$ is independently a saturated or unsaturated alkyl or alkylene radical containing 12 to 22 carbon atoms;

$Q^{21a}$ and $Q^{21b}$ are alkyl containing 1 to 4 carbon atoms or benzyl, —$CH_2CH_2OH$, or —$CH_2CH(OH)CH_3$, or $Q^{21a}$ can be $R^{21}$—$C(O)$—$(O-Alk^{21}))_{1-4}$—;

each $Alk^{21}$ is independently $C_2H_4$ or $C_3H_6$ or $C_4H_8$.

each $R^{23}$ is independently straight or branched alkyl or alkenyl containing 8 to 22 carbon atoms;

$R^{23a}$ is straight or branched alkyl or hydroxyalkyl containing 1 to 3 carbon atoms, benzyl, or —$C_2H_4OC(O)$ $R_4$ wherein $R_4$ is straight or branched alkyl or alkenyl containing 8 to 22 carbon atoms;

$R^{23b}$ is H, —$CH_3$, —$C_2H_5$ or benzyl; and

X is an anion.

20. A process according to claim 19 wherein R is branched noncyclic alkylene containing 7 to 12 carbon atoms.

21. A process according to claim 19 wherein R is branched noncyclic alkylene containing 7 to 9 carbon atoms.

22. A process in accordance with claim 19 wherein said nonionic component comprises one or both of 2,2,4-trimethyl-1,3-pentane diol and 2-ethylhexane-1,3-diol.

23. A process in accordance with claim 19 wherein said nonionic component comprises 2,2,4-trimethyl-1,3pentane diol.

* * * * *

UNITED STATES PATENT AND TRADEMARK OFFICE
CERTIFICATE OF CORRECTION

PATENT NO. : 5,753,079
DATED : May 19, 1998
INVENTOR(S) : Neil A. Jenny, et al.

It is certified that error appears in the above-indentified patent and that said Letters Patent is hereby corrected as shown below:

Column 7, line 52: ")$^{-2}$" should read --)$^{+2}$--

Column 7, line 53: "R$^2$" should read --R$^1$--

Column 7, line 65: "A$_O$" should read --A$^O$--

Column 8, line 9: "A$_O$" should read --A$^O$--

Column 13, line 2: "R$_{24A}$, R$^{24b}$, R$_{24c}$, and R$^{24d}$ or R$_{24e}$ is R$^A$C" should read --R$^{24a}$, R$^{24b}$, R$^{24c}$, and R$^{24d}$ or R$^{24e}$ is R$^A$C --

Column 20, line 19, Claim 23: "3pentane" should read --3-pentane--

Signed and Sealed this

Tenth Day of April, 2001

Attest:

NICHOLAS P. GODICI

*Attesting Officer*  Acting Director of the United States Patent and Trademark Office